United States Patent
Guo et al.

(10) Patent No.: US 10,238,776 B2
(45) Date of Patent: Mar. 26, 2019

(54) HYDROPHOBIC CATHETER AND COMPOSITION

(75) Inventors: Xiaoping Guo, Eden Prairie, MN (US); James V. Kauphusman, Newport Beach, CA (US); David P. Johnson, Brooklyn Park, MN (US); Karen L. Armstrong, Maple Plain, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1008 days.

(21) Appl. No.: 12/981,292

(22) Filed: Dec. 29, 2010

(65) Prior Publication Data
US 2012/0172840 A1 Jul. 5, 2012

(51) Int. Cl.
A61L 29/08 (2006.01)
A61M 25/00 (2006.01)

(52) U.S. Cl.
CPC .......... *A61L 29/085* (2013.01); *A61L 2420/08* (2013.01); *A61M 25/0012* (2013.01)

(58) Field of Classification Search
CPC .............. A61L 29/085; A61L 2420/08; A61M 25/0012
USPC .......................................... 604/239, 523–527
See application file for complete search history.

(56) References Cited

U.S. PATENT DOCUMENTS

| | | | |
|---|---|---|---|
| 4,876,126 A | 10/1989 | Takemura et al. | |
| 5,109,861 A | 5/1992 | Walinsky et al. | |
| 5,419,374 A | 5/1995 | Nawrot et al. | |
| 5,569,218 A * | 10/1996 | Berg ................. | A61M 25/0009 138/134 |
| 5,627,079 A | 5/1997 | Gardella, Jr. et al. | |
| 5,662,622 A | 9/1997 | Gore et al. | |
| 5,704,908 A * | 1/1998 | Hofmann et al. .............. | 604/21 |
| 5,795,939 A | 8/1998 | Lorek | |
| 5,932,299 A | 8/1999 | Katoot | |
| 5,939,492 A | 8/1999 | Lorek | |
| 6,041,826 A | 3/2000 | Lorek et al. | |
| 6,096,369 A | 8/2000 | Anders et al. | |
| 6,143,415 A | 11/2000 | Lorek et al. | |

(Continued)

FOREIGN PATENT DOCUMENTS

| | | |
|---|---|---|
| EP | 0558373 | 10/1995 |
| EP | 0726926 | 2/1998 |

(Continued)

OTHER PUBLICATIONS

"International Search Report & Written Opinion", PCT/US2011/059115 dated Feb. 15, 2012.

(Continued)

*Primary Examiner* — Bradley J Osinski
(74) *Attorney, Agent, or Firm* — Wiley Rein LLP

(57) ABSTRACT

In various embodiments, a surgical catheter is provided. The catheter may comprise one or more hydrophobic barrier layers made from an ethylene-pertfluoroethylenepropylene ("EFEP") copolymer. Additionally, the catheter may comprise another polymer layer made from a reactive polar polymer. In at least one embodiment, the reactive polar polymer may be a modified-poly(ether block amide) ("PEBA") copolymer, such as an amine-terminated PEBA. Moreover, in various embodiments, a composition is provided that may comprise a reactive polar polymer bonded to an EFEP copolymer.

15 Claims, 6 Drawing Sheets

(56) References Cited

U.S. PATENT DOCUMENTS

| | | | |
|---|---|---|---|
| 6,165,166 | A | 12/2000 | Samuelson et al. |
| 6,500,532 | B1 | 12/2002 | Ruefer et al. |
| 6,616,982 | B2 | 9/2003 | Merrill et al. |
| 6,824,553 | B1* | 11/2004 | Samson ............. A61M 25/005 606/192 |
| 6,911,509 | B1 | 6/2005 | Chung et al. |
| 7,220,807 | B2 | 5/2007 | Chung et al. |
| 7,758,892 | B1* | 7/2010 | Chen et al. .................. 424/497 |
| 7,777,075 | B2 | 8/2010 | Ishikawa et al. |
| 8,216,498 | B2 | 7/2012 | Quillin |
| 2002/0134451 | A1* | 9/2002 | Blasko et al. ............... 138/140 |
| 2005/0004560 | A1 | 1/2005 | Cox |
| 2005/0074570 | A1 | 4/2005 | Agrawal |
| 2005/0074605 | A1 | 4/2005 | Agrwal |
| 2005/0107870 | A1 | 5/2005 | Wang |
| 2005/0118372 | A1 | 6/2005 | Bonnet et al. |
| 2006/0083882 | A1 | 4/2006 | Schmitz |
| 2006/0198976 | A1 | 9/2006 | Trapp |
| 2007/0005024 | A1 | 1/2007 | Weber |
| 2008/0234811 | A1 | 9/2008 | Kitching |
| 2009/0131884 | A1 | 5/2009 | Yamada |
| 2009/0163851 | A1* | 6/2009 | Holloway et al. ............. 604/22 |
| 2009/0171319 | A1 | 7/2009 | Guo et al. |
| 2009/0188578 | A1 | 7/2009 | Bonnet et al. |
| 2009/0326647 | A1 | 12/2009 | Quillin |
| 2010/0063476 | A1 | 3/2010 | Quillin |
| 2010/0217235 | A1 | 8/2010 | Thorstenson et al. |
| 2010/0228348 | A1 | 9/2010 | McClain |
| 2010/0280452 | A1 | 11/2010 | Chen et al. |
| 2012/0172840 | A1 | 7/2012 | Guo et al. |

FOREIGN PATENT DOCUMENTS

| | | |
|---|---|---|
| EP | 0696301 | 12/1998 |
| EP | 0740754 | 3/1999 |
| JP | 93/095892 A | 4/1993 |
| JP | 1993-095892 | 4/1993 |
| JP | H1-033181 | 2/1998 |
| JP | 2007-000392 | 1/2007 |
| JP | 2007537827 | 12/2007 |
| WO | 00/059963 A1 | 10/2000 |
| WO | 2000/059963 | 10/2000 |
| WO | 01/017575 A1 | 3/2001 |
| WO | 2001/017575 | 3/2001 |
| WO | 03/066121 A1 | 8/2003 |
| WO | 2003/066121 | 8/2003 |
| WO | 04/000384 A1 | 12/2003 |
| WO | 2004000384 | 12/2003 |
| WO | WO2005115496 | 12/2005 |
| WO | 06/023261 A2 | 3/2006 |
| WO | 2006/023261 | 3/2006 |
| WO | 07/025293 A2 | 3/2007 |
| WO | 2007/025293 | 3/2007 |
| WO | 07/114890 A2 | 10/2007 |
| WO | 2007/114890 | 10/2007 |
| WO | 09/158485 A2 | 12/2009 |
| WO | 2009/158485 | 12/2009 |
| WO | 2012/091794 | 7/2012 |

OTHER PUBLICATIONS

Supplementary European Search Report for EP 11 85 2471 dated Aug. 21, 2014.

Onder, S. et al. "Alteration of PTFE Surface to Increase Its Blood Compatibility," J Biomater Sci Polym Ed., Jun. 30, 2010.

* cited by examiner

HYDROPHOBIC CATHETER AND COMPOSITION

BACKGROUND OF THE INVENTION a. Field of the Invention

The present disclosure is directed toward medical devices, such as catheters. In particular, the present disclosure relates to catheters comprising one or more hydrophobic barrier layers. Additionally, the present disclosure is directed to compositions having hydrophobic properties.

b. Background Art

Catheters are used for an ever-growing number of procedures. For example, catheters are used for diagnostic, therapeutic, and ablative procedures, to name just a few examples. In an electrophysiology ("EP") procedure, for example, a catheter may be manipulated through the patient's vasculature and to an intended site, for example, a site within the patient's heart. A catheter may carry one or more devices, sensors, or surgical instruments, such as electrodes, which may be used for ablation, diagnosis, and/or the like.

During a procedure, a catheter may be exposed to an aqueous environment comprising blood and/or other bodily fluids within the patient's vasculature and/or heart, for example. The mechanical and material properties of a catheter should remain constant during such a procedure and not be affected by the environment contacting the catheter so that the catheter's operator can rely on its response and performance at any point throughout the procedure.

The foregoing discussion is intended only to illustrate the field and background of the present disclosure and should not be taken as a disavowal of claim scope.

BRIEF SUMMARY OF THE INVENTION

In various embodiments, a catheter is provided. In at least one embodiment, the catheter can comprise a first polymer layer bonded to a second polymer layer. In these embodiments, the second polymer layer can comprise an ethylene-perfluoroethylenepropylene ("EFEP") copolymer.

In at least one embodiment, the catheter can comprise a first polymer layer bonded to a second polymer layer. In these embodiments, the first polymer layer can comprise a reactive polar polymer.

In various embodiments, a method of manufacturing a catheter is provided. In at least one embodiment, the method can comprise the steps of extruding a first polymer to form a first polymer layer and then extruding a second polymer onto the first polymer layer. In these embodiments, the second polymer can comprise an EFEP copolymer.

In at least one embodiment, the method can comprise the steps of extruding a first polymer to form a first polymer layer and then extruding a second polymer onto the first polymer layer. In these embodiments, the second polymer can comprise a reactive polar polymer.

In at least one embodiment, the method can comprise the step of co-extruding a first polymer with a second polymer to form a first polymer layer and a second polymer layer. In these embodiments, the second polymer can comprise an EFEP copolymer.

In at least one embodiment, the method can comprise the step of co-extruding a first polymer with a second polymer to form a first polymer layer and a second polymer layer. In these embodiments, the first polymer can comprise a reactive polar polymer.

In various embodiments, a composition is provided. The composition can comprise a reactive polar polymer bonded to an EFEP copolymer.

The foregoing and other aspects, features, details, utilities, and advantages of the present invention will be apparent from reading the following description and claims, and from reviewing the accompanying drawings.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present disclosure is defined solely by the claims. The features illustrated or described in connection with one exemplary embodiment may be combined with the features of other embodiments. Such modifications and variations are intended to be included within the scope of the present disclosure.

Figure 1:
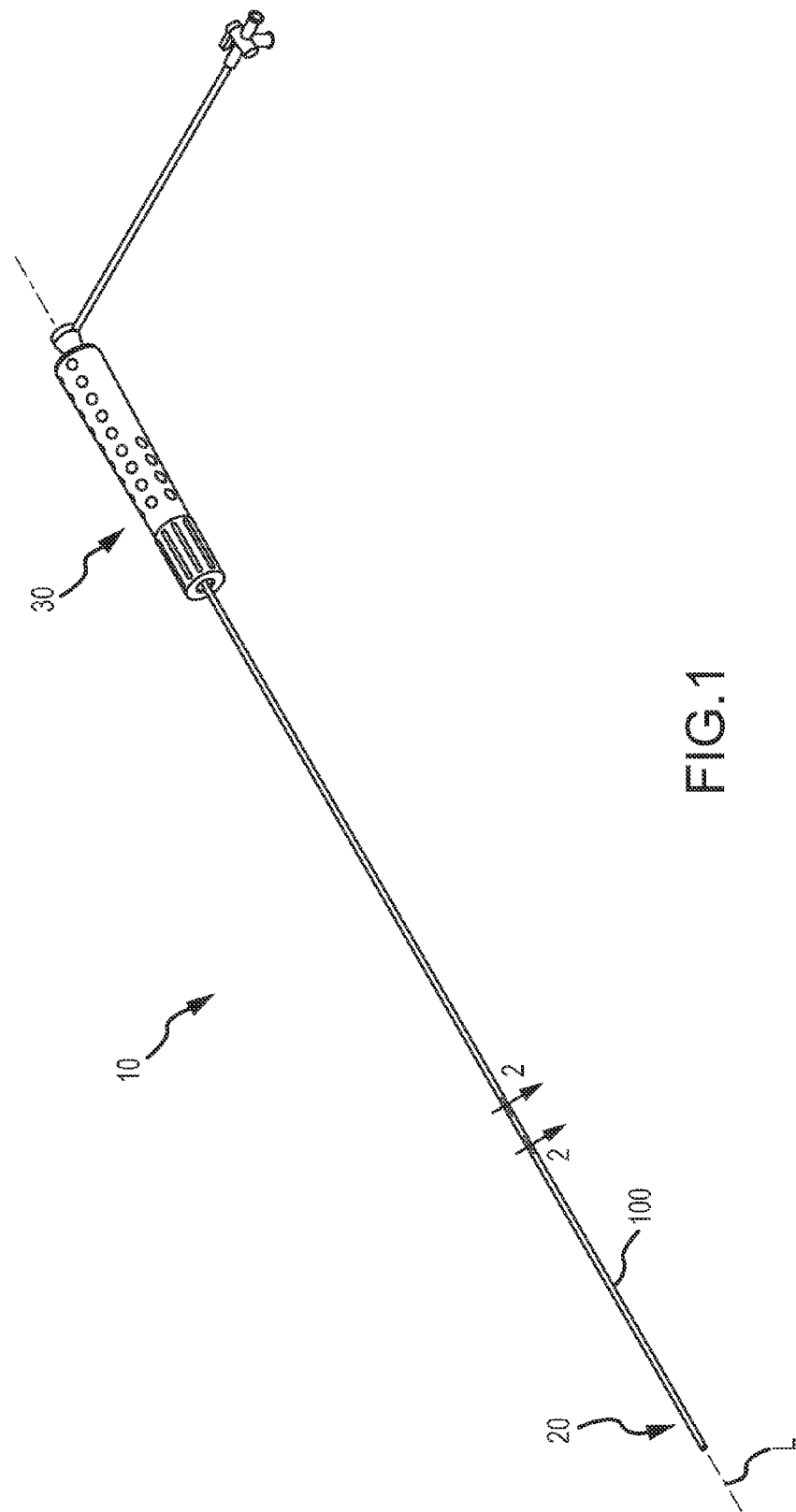
FIG. 1 is perspective view of a catheter, according to a non-limiting embodiment.

Referring now to the drawings wherein like reference numerals are used to identify identical or similar components in the various views, FIG. 1 illustrates a catheter embodiment of a medical device for use in connection with a number of diagnostic and therapeutic procedures performed, for example, within the heart of a human being or an animal. For clarity and brevity purposes, the description below will be directed primarily to a medical device, such as catheter 10, that comprises a shaft, such as shaft 100, for use in cardiac applications. It will be appreciated by those having ordinary skill in the art, however, that the description below may be applicable to medical devices and apparatuses other than catheters, and for catheters, medical devices, and apparatuses used in connection with applications other than cardiac applications. Accordingly, apparatuses and medical devices other than catheters and apparatuses, medical devices, and catheters for use in applications other than cardiac applications remain within the spirit and scope of the present disclosure. Additionally, as used herein, a "catheter" means an elongated structure that can be inserted into and/or through a body cavity, duct, and/or vessel. In at least one embodiment, a catheter may be hollow and/or define a lumen therethrough for passing another medical device, such as a guidewire or another catheter, for example. However, in various embodiments, a catheter may be closed at least at its distal end.

With reference to FIG. 1, in an exemplary embodiment, the catheter 10 comprises a distal portion 20 and a proximal portion 30. The distal portion 20 may further comprise a shaft 100 that is configured to be at least partially inserted into and/or through a body passage or another anatomic structure, such as a human patient's vasculature, including a blood vessel. The distal portion 20 may also comprise one or more electrodes or other therapeutic, diagnostic, and/or navigational features located on, in, and/or next to the shaft 100. The proximal portion 30 may comprise a handle and controls for manipulating the distal portion 20 and/or shaft 100. Additionally, as discussed in more detail below, the shaft 100 may generally be a tubular structure comprising inner and outer polymeric layers and, optionally, have metallic braids layered in between (see catheter shafts 100''' and 100'''' in FIGS. 5 and 6 and discussed below, for example). The shaft 100 may also define one or more lumens, such as lumen 140 (see FIG. 2). The shaft 100 and/or lumen 140 may be configured to deliver one or more items, such as energy, fluid, and/or another medical device, to the distal portion 20 and/or shaft 100. The lumen 140 may define a longitudinal axis "L" and may be sized and configured to receive a medical device therein. Further, the shaft 100 may have a straight configuration, or alternatively, may have a fixed curved shape/configuration. Additional details regarding exemplary catheters and/or medical devices may be found in one or more of U.S. application Ser. No. 11/647,313, entitled STEERABLE CATHETER USING FLAT PULL WIRES AND METHOD OF MAKING SAME, U.S. application Ser. No. 11/617,524, entitled VIRTUAL ELECTRODE ABLATION CATHETER WITH ELECTRODE TIP AND VARIABLE RADIUS CAPABILITY, and/or U.S. application Ser. No. 11/170,550, entitled ACTUATION HANDLE FOR A CATHETER, each incorporated by reference in its entirety herein.

Figure 2:
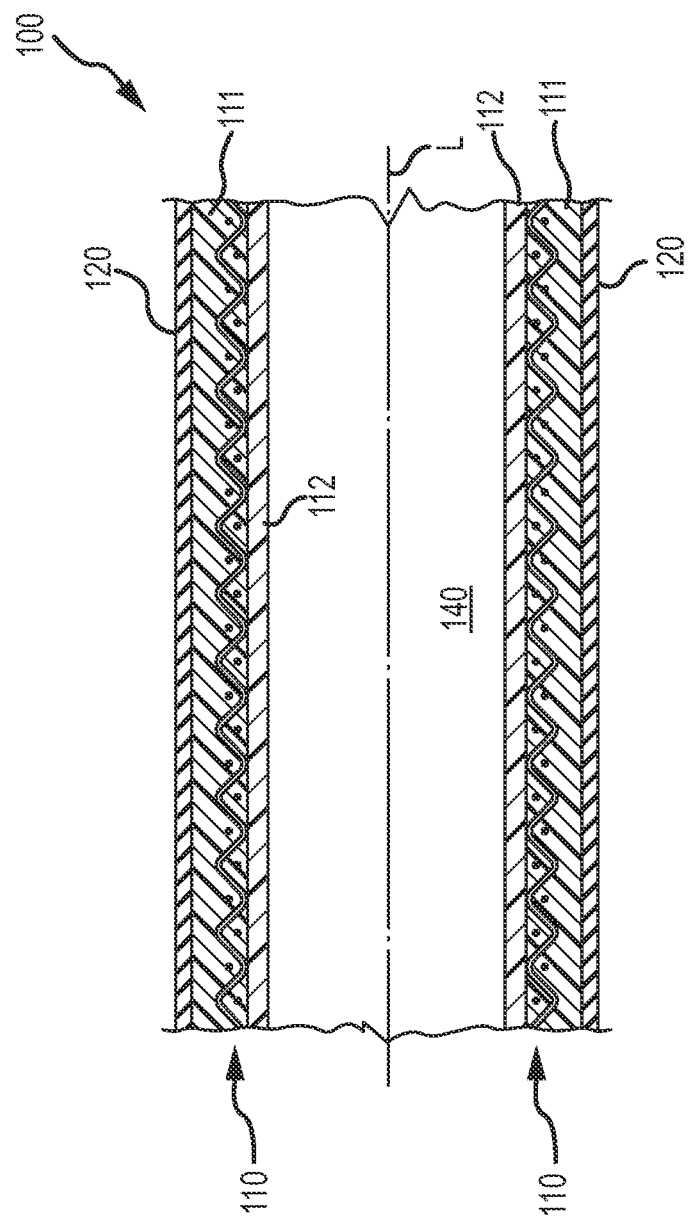
FIG. 2 is partial cross-sectional view of a portion of a shaft of the catheter of FIG. 1, taken along line 2-2 as shown in FIG. 1.

Referring now to FIG. 2, a partial cross-sectional view of a portion of the shaft 100 of the catheter of FIG. 1, taken along line 2-2 or longitudinal axis L is shown. In at least one embodiment, the catheter shaft 100 may comprise an inner polymer layer, such as first polymer layer 110, bonded to an outer polymer layer, such as second polymer layer 120. As shown, the first polymer layer 110 may comprise a set of sub-layers, such as an outer polymeric layer 111 and an inner polymeric layer 112. To obtain chemical bondability between the first polymer layer 110 and the second polymer layer 120, the polymeric materials used for making these layers should be chemically compatible, and this may limit the types of polymeric materials available to use in combination with one another.

In current industrial practices, the base polymers typically used to construct the inner and outer layers of a catheter shaft body are selected from materials having compatible processing methods and conditions, such as polar thermoplastics, including polyamides or nylons (namely nylon 11, nylon 12, nylon 612, nylon 6, nylon 66, etc.), polyurethanes, polyesters (namely poly(ethylene terephthlate), poly(butylene terephthlate), etc.), poly(bisphenol-A carbonate), and the like: Thermoplastic elastomers with material chemistries based on polyether-type soft segments and polyamide-, polyurethane-, or polyester-type hard segments are quite commonly used for the construction of various catheter shafts due to their chemical compatibility and wide spectrum of mechanical properties among different grades of the respective classes. However, non-polar polymeric materials, like typical polyolefins and fluoropolymers, are seldom used for the construction of catheter shafts, because they are inherently inert and not chemically compatible with other polymeric materials. In some catheter shaft designs, a typical fluoropolymer, such as polytetrafluoroethylene ("PTFE"), may be used as the catheter shaft liner for the purpose of reducing surface friction, if the PTFE surface that is in contact with another polymeric material is chemically activated using an inconvenient surface treatment such as chemical etching. This is at least partly due to the observation that PTFE cannot be melt-extruded, unlike the polymer(s) of the first and second polymer layers 110, 120, described below.

Continuing, according to various embodiments, the first polymer layer 120 may comprise a polar polymer. For example, the outer polymeric layer 111 and/or the inner polymeric layer 112 may comprise a polar polymer. In such embodiments, the outer polymeric layer 111 and/or the inner polymeric layer 112 may comprise one or more of the following: polar thermoplastics, including polyamides or nylons (namely nylon 11, nylon 12, nylon 612, nylon 6, nylon 66, etc.), polyurethanes, polyesters (namely poly(ethylene terephthlate), poly(butylene terephthlate), etc.), poly(bisphenol-A carbonate), and the like; and thermoplastic elastomers with material chemistries based on polyether-type soft segments and/or polyamide-, polyurethane-, or polyester-type hard segments, such as poly(ether block amide) ("PEBA") copolymers, for example.

The second polymer layer 120 may form a hydrophobic barrier layer and may comprise a fluorine-containing polymer ("FCP") which may be a hydrophobic FCP, or a melt-processable thermoplastic fluoropolymer. Exemplary FCPs include, but are not limited to, poly(vinylidene fluoride) ("PVDF") and/or ethylene-perfluoroethylenepropylene ("EFEP") copolymer. In at least one embodiment, the FCP may be functionalized such that the FCP binds to one or more polar polymers, such as the polar polymer(s) of the first polymer layer 110, for example. In such embodiments, the FCP may have one or two modified ending groups, —X and/or —Y. Such a functionalized FCP may have the following generalized chemical formula:

Figure 7:
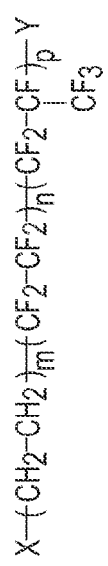
FIG. 7 is a chemical formula of a non-limiting embodiment of a terminally-functionalized ethylene-perfluoroethylenepropylene ("EFEP") copolymer.

As noted above, in at least one embodiment, the second polymer layer 120 may comprise EFEP copolymer. In various embodiments, the EFEP copolymer may comprise a functionalized EFEP copolymer and/or a terminally-functionalized EFEP copolymer. As used herein, "termination" refers to the addition of one or more reactive functional groups to one or more ends of a polymer chain, as contrasted by "grafting," which refers to the addition of reactive functional groups to one or more non-ends or mid-chain locations of a polymer chain during chemical modification of the polymer. The chemical formula for such a terminally-functionalized EFEP copolymer can be seen in FIG. 7 and is also shown below:

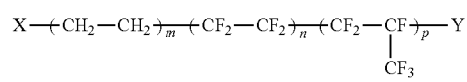

The letters m, n, and p represent natural numbers and the functional end groups, —X and —Y, can also be seen. According to various embodiments, the end functional groups, —X and/or —Y, may include, but are not limited to carboxyl groups, carbonate groups, carboxyl halide groups, and/or carbonyl halide groups.

In more detail, according to at least one embodiment, exemplary carboxyl groups may have the following formula:

—C(=O)O—R

Also, exemplary carbonate groups, according to at least one embodiment, may have the following formula:

—OC(=O)O—R

In the foregoing chemical formulas for carboxyl and carbonate groups, R may be a hydrogen atom or an organic group, like an alkyl group with 1 to 30 carbon atoms or alkyl groups with 2 to 30 carbon atoms and an ether coupling, for example. Exemplary carbonate groups include the following:

—OC(=O)OCH$_3$

—OC(=O)OC$_4$H$_9$

—OC(=O)OCH$_2$CH$_2$—O—CH$_2$CH$_2$CH$_3$

Additionally, in at least one embodiment, exemplary carboxyl halide groups may have the following formula:

—C(=O)O—Z where Z is a halogen atom, such as chlorine, fluorine, and the like. Exemplary carboxyl halide groups therefore may include the following:

—C(=O)OCl

—C(=O)OF

Lastly, in at least one embodiment, exemplary carbonyl halide groups may have the following formula:

—CO—Z where Z is a halogen atom, such as chlorine, fluorine, and the like. Exemplary carbonyl halide groups therefore may include the following:

—COCl

—COF

Briefly, an EFEP copolymer generally results from the copolymerization of tetrafluoroethylene ("TFE"), hexafluoropropylene ("HFP"), and ethylene monomers at different mole percentages via different polymerization techniques. For example, an EFEP copolymer may contain 20 to 90 mole percentage of TFE; 10 to 80 mole percentage of ethylene; and 1 to 70 mole percentage of HFP. In various embodiments, a functionalized EFEP copolymer as described above may contain, in addition to the monomer units contributed by TFE, HFP, and ethylene, one or more types of other monomers. These additional monomer(s) may be chosen such that the resulting EFEP copolymer maintains its inherent hydrophobicity. In at least one embodiment, for the convenience of melt processing during the making of a catheter shaft, for example, such EFEP copolymers may have relatively low melting points, which may be between approximately 160° C. and 240° C. as measured by a differential scanning calorimeter ("DSC"), for instance. In various embodiments, the functionalized FCP, such as terminally-functionalized EFEP copolymer, may be semi-crystalline and have a melting point lower than about 250° C., and in at least one embodiment, may have a melting point lower than about 220° C. Examples of functionalized EFEP copolymers currently available from commercial sources are the NEOFLON™ RP series resins (Daikin America, Inc., Orangeburg, N.Y., USA). Additional details regarding EFEP copolymers, including terminally-functionalized EFEP copolymers, and their manufacture may be found in U.S. Pat. No. 6,911,509, entitled FUNCTIONAL FLUOROPOLYMERS AND PROCESS THEREFOR, and/or U.S. Pat. No. 7,220,807, entitled PROCESS OF PREPARING FUNCTIONAL FLUOROPOLYMERS, incorporated herein by reference in their entireties.

Referring again to FIG. 2, according to various embodiments, the first polymer layer 110 may comprise a reactive polar polymer. As used herein, a "reactive polar polymer" is a composition of one or more polymers that may directly and/or covalently bind to a non-polar polymer, such as a FCP, like an EFEP copolymer and/or a terminally-functionalized EFEP copolymer, for example. In at least one embodiment, the reactive polar polymer may comprise an amine-rich or amine-terminated polar polymer, such as a polyamide/nylon, a polyurethane, a polyester, a related thermoplastic elastomer, and/or the like that is/are amine-terminated. Additionally, in at least one embodiment, the amine-terminated polar polymer may comprise an amine-terminated poly(ether block amide) ("PEBA") or polyamide, for instance. An exemplary modified or amine-terminated PEBA may include VESTAMID® BS-1144 and/or BS-1145 sold by Evonik Degussa GmbH (Essen, Germany). An exemplary modified or amine-terminated polyamide may include VERSAMID® 728 sold by Cognis Corporation (Cincinnati, Ohio, USA). Alternatively, the reactive polar polymer may comprise a thermoplastic polyurethane. While the reactive polar polymer may be reactive due to being terminated or grafted with one more amine functional groups, other functional groups, such as oxazoline or epoxy, for example, may render the polar polymer reactive.

Referring still to FIG. 2, owing to the terminally-functionalized EFEP copolymer in the second polymer layer 120 and/or the reactive polar polymer in the first polymer layer 110, the first polymer layer 110 may be directly bonded to the second polymer layer 120. In at least one embodiment, the first polymer layer 110 may be covalently bonded to the second polymer layer 120. Additionally, in at least one embodiment, the reactive polar polymer, as discussed above, of the first polymer layer 110, may generate good melt adhesion during a melt process, as discussed below, with the terminally-functionalized EFEP copolymer of the second polymer layer 120 due to interfacial chemical reactions between, for example, amine- and carbonate-functional groups of the reactive polar polymer and the EFEP copolymer, respectively, in the (co-)extruded polymers at high melt temperatures.

Figure 3:
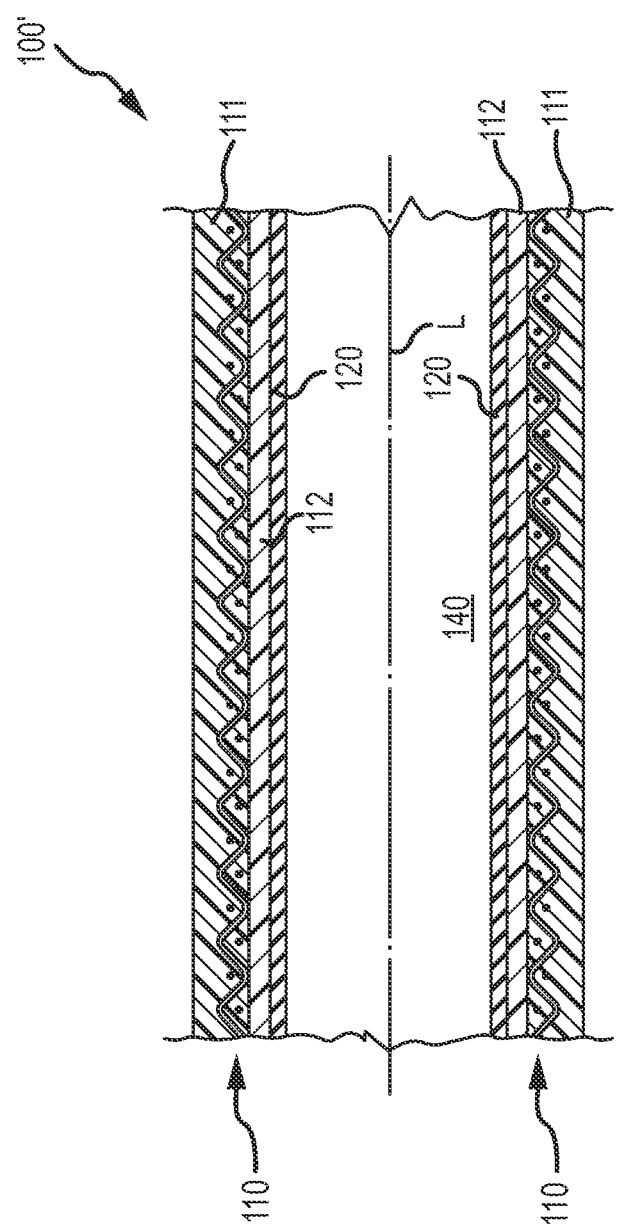
FIG. 3 is a partial cross-sectional view of a portion of a catheter shaft, according to a first non-limiting embodiment.
Figure 4:
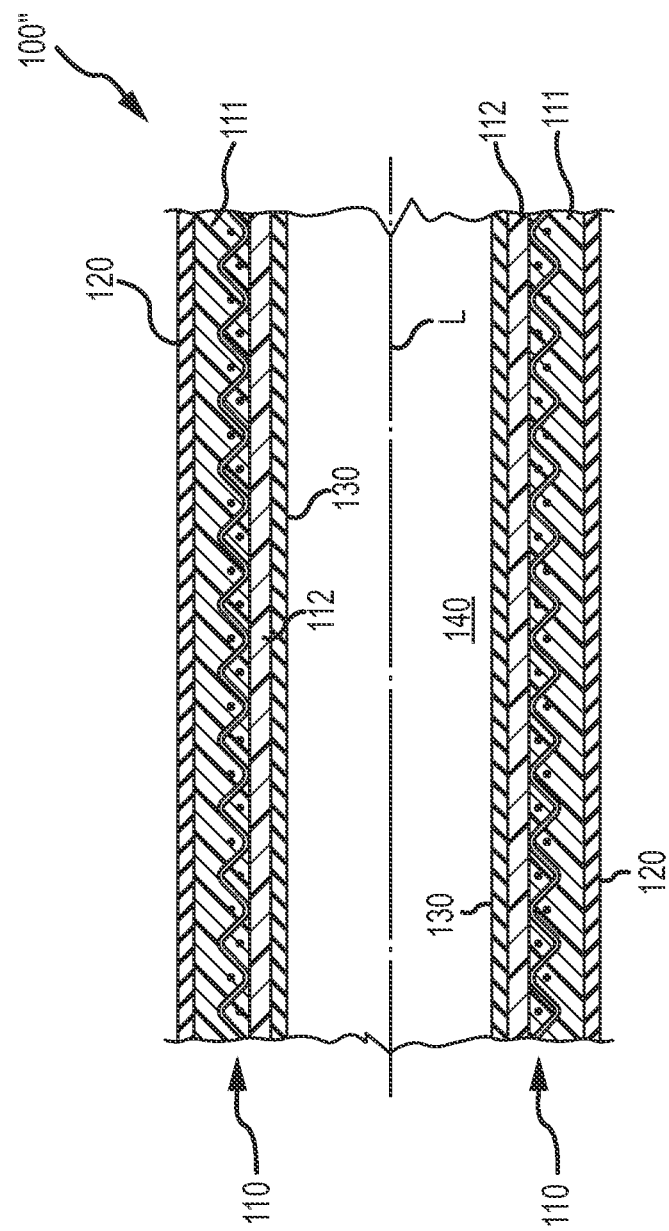
FIG. 4 is a partial cross-sectional view of a portion of a catheter shaft, according to a second non-limiting embodiment.

A hydrophobic barrier layer, such as one comprising EFEP copolymer, may be applied to various portions of a catheter or medical device. For example, as shown in FIG. 2, the second polymer layer 120 may form an outer or outermost layer of the catheter shaft 100, thereby providing an outer layer comprising an EFEP copolymer. Alternatively, referring to FIG. 3, the second polymer layer 120 may form an inner or innermost layer of a catheter shaft 100', which is generally similar to catheter shaft 100. Additionally, in at least one embodiment and as shown in FIG. 4, a catheter shaft 100" (also generally similar to catheter shaft 100) may further comprise, in addition to the outer or second polymer layer 120, an inner or third polymer layer 130 bonded to the intermediate or first polymer layer 110. Like the second polymer layer 120, the third polymer layer 130 may also comprise EFEP copolymer. Moreover, as with the hydrophobic barrier layer or second polymer layer 120, described above, the EFEP copolymer may be functionalized such that the functionalized EFEP copolymer in the third polymer layer 130 and the reactive polar polymer in the first polymer layer 110 may be directly and/or covalently bonded together.

Figure 5:
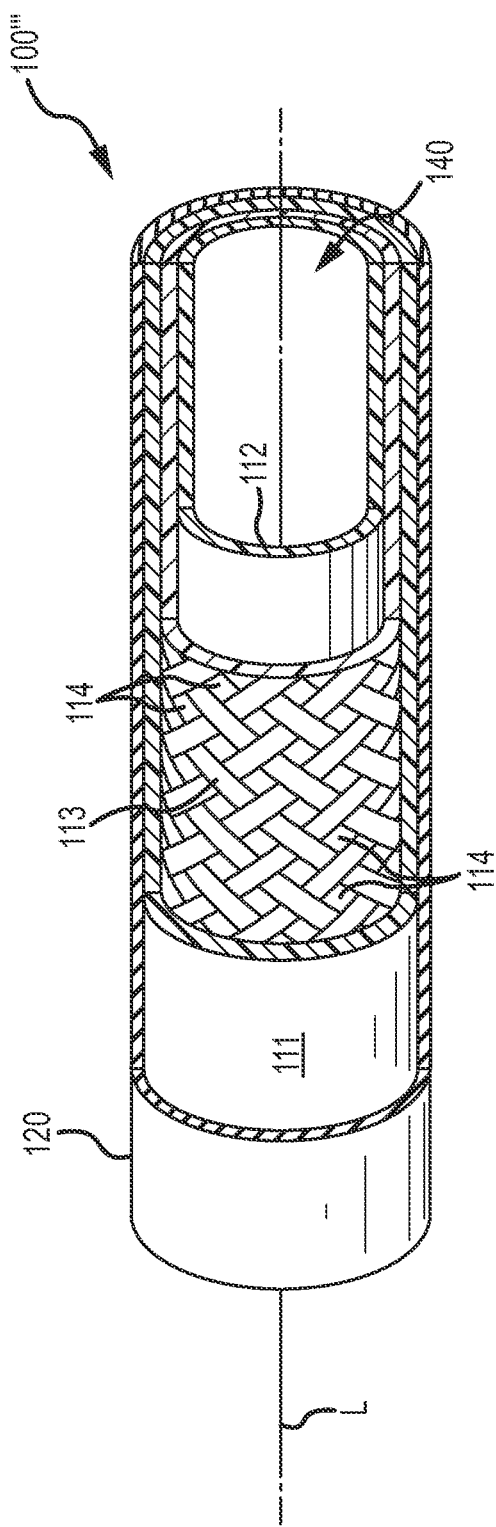
FIG. 5 is a partial cut-away view of a portion of a catheter shaft, according to a third non-limiting embodiment.

In at least one embodiment and as mentioned above, a catheter shaft generally similar to catheter shaft 100, such as shaft 100''' seen in FIG. 5, may further comprise a metallic braided layer 113 between the outer polymeric layer 111 and the inner polymeric layer 112. Such a metallic braided layer 113 may provide additional hoop strength to the catheter shaft 100' while still permitting the shaft 100' to be flexible or compliant. Owing to the braid pattern, openings 114 may be defined within the metallic braided layer. Through the braid openings 114, the outer polymeric layer 111 may bind or adhere to the inner polymeric layer 112. Moreover, the outer polymeric layer 111 may bind or adhere to the metallic braided layer 113 itself. Additionally, as discussed above, the hydrophobic barrier layer 120 may comprise functionalized EFEP copolymer such that it may be directly and/or covalently bonded to the reactive polar polymer in the outer polymeric layer 111.

Figure 6:
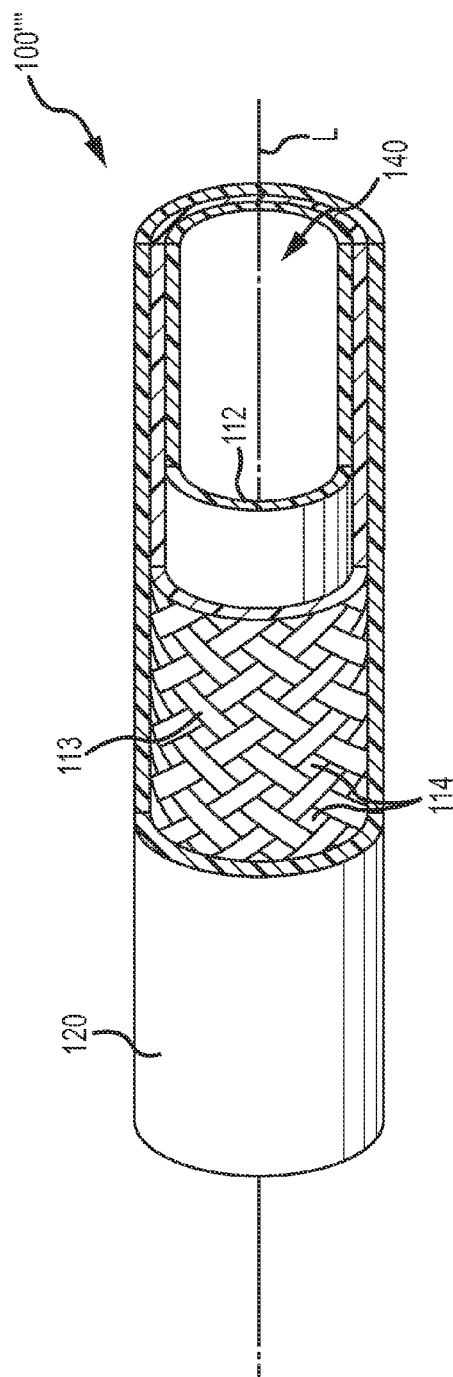
FIG. 6 is a partial cut-away view of a portion of a catheter shaft, according to a fourth non-limiting embodiment.

In at least one embodiment, a catheter shaft generally similar to catheter shaft 100, such as shaft 100'''' seen in FIG. 6, may not have an outer polymeric layer (such as layer 111 seen in FIG. 5) between the hydrophobic barrier layer 120 and the inner polymeric layer 112. In other words, the hydrophobic barrier layer 120 may be directly bonded to the inner polymeric layer through the braid openings 114 and/or to the metallic braided layer 113. As discussed above, the hydrophobic barrier layer 120 may comprise functionalized EFEP copolymer such that it may be directly and/or covalently bonded to the reactive polar polymer in the inner polymeric layer 112.

Various methods may be employed to produce a catheter shaft, such as catheter shaft 100, described above. In various embodiments, a melt process, such as mono-extrusion, sequential extrusion, co-extrusion, and/or heat lamination (reflow), and the like may be utilized to produce the catheter shaft. In more detail, two such catheter shaft manufacturing processes are sequential mono-extrusion and heat lamination, or reflow. In the sequential mono-extrusion shaft manufacturing process, the inner polymeric layer is first extruded over a continuous, supportive core rod having a melting temperature higher than that of the extrusion temperature of the layer. Then, a metallic mesh in a given weaving pattern is introduced onto the inner layer via braiding. Next, the outer polymeric layer, or the "overlayer," is then over-extruded onto the braided inner polymer layer.

In the reflow catheter shaft manufacturing process, the inner and outer polymeric layers of tubular structure are prepared via polymer extrusion processes. Then, a metallic mesh in a given weaving pattern is pre-made via braiding. The inner layer, the metallic braiding, and the outer layer are then layer-by-layer introduced onto a supportive, metallic core rod and incorporated into a single, cylindrical, shaft body via a heat lamination, or reflow, processes by applying an external heat source over a proper shrink tube that completely and circumferentially embraces the shaft body to be formed. As potentially desired by end-use performances for such a catheter shaft of composite structure, including clinical deliverability in the tortuous human anatomy, the inner and outer polymeric layers may be chemically bondable under pressure and heat. The two layers may largely contain the metallic braids in between, and ideally be bonded onto and/or through the layer of the metallic braids. As such, the contained braids of the bonded polymeric layers may provide some reinforcing effects for the shaft body in terms of column strength, fracture energy, and/or kink resistance, and the like, for example.

Accordingly, in at least one embodiment, referring to FIG. 2, for example, a catheter shaft 100 may be manufactured using a sequential extrusion or a sequential mono-extrusion technique. In such an embodiment, a first polymer, such as an amine-terminated PEBA, is extruded to form the first polymer layer 110 and a second polymer, such as an EFEP copolymer (which may be terminally-functionalized), is then extruded onto the first polymer layer 110 to form the second polymer layer 120. The mono-extrusion process may be carried out with a regular single-screw extruder. As discussed above, the first polymer layer 110 may comprise outer and inner polymeric layers 111 and 112, respectively. As shown in FIG. 2, the hydrophobic barrier layer or second polymer layer 120 may form an outer layer of the catheter shaft 100 that is bonded, directly and/or covalently, for example, to the outer polymeric layer 111 of the first polymer layer 110. The heat energy of the extrusion process and/or the reflow/heat lamination process, if such is applied, may assist in forming such a direct and/or covalent bond between the second polymer layer 120 and outer polymeric layer 111. Alternatively, referring to FIG. 3, the second polymer layer 120 may form the inner layer of the catheter shaft 100' that is bonded, directly and/or covalently, for example, to the inner polymeric layer 112 of the first polymer layer 110. Again, the heat energy of the extrusion process and/or the reflow/heat lamination process, if such is applied, may assist in forming such a direct and/or covalent bond between the second polymer layer 120 and inner polymeric layer 112. Further, in at least one embodiment and referring to FIG. 4, another hydrophobic barrier layer or third polymer layer 130 may be formed by extruding a third polymer, such as an EFEP copolymer (which may be the same or similar as the second polymer discussed above), before or after the extrusion steps that create the first and/or second polymer layers 110 and 120, respectively. In such an embodiment, hydrophobic barrier layers 120 and 130 may form the interior and exterior layers of the catheter shaft 100'' and may both be directly and/or covalently bonded to the layers 111, 112, respectively, of the first polymer layer 110. Again, the heat energy of the extrusion process and/or the reflow/heat lamination process, if such is applied, may assist in forming such a direct and/or covalent bond between the second polymer layer 120 and outer polymeric layer 111 and between the third polymer layer 130 and the inner polymeric layer 112. Additionally, in at least one embodiment and referring to FIG. 5, the inner polymeric layer 112 of catheter shaft 100''' may be first extruded and then a metallic braided layer 113 may be formed by braiding stainless steel flat wire, for example, onto the inner polymeric layer 112. In such an embodiment, the outer polymeric layer 111 may be formed by extruding a polymer, such as an amine-terminated PEBA, for example, onto the metallic braided layer and thereafter another polymer, such as an EFEP copolymer (which may be terminally-functionalized), may be extruded to form the hydrophobic barrier layer 120 that may be bonded, directly and/or covalently, for example, to the outer polymeric layer 111, as discussed above. Again, the heat energy of the extrusion process and/or the reflow/heat lamination process, if such is applied, may assist in forming such a direct and/or covalent bond between the hydrophobic barrier layer 120 and the outer polymeric layer 111. Lastly, in at least one embodiment and referring to FIG. 6, the inner polymeric layer 112 of catheter shaft 100'''' may be first created by extruding a first polymer, such as an amine-terminated PEBA, for example, and then a metallic braided layer 113 may be formed by braiding stainless steel flat wire, for example, onto the inner polymeric layer 112. Thereafter, the hydrophobic barrier layer 120 may be formed by directly extruding a polymer, such as EFEP copolymer (which may be terminally-functionalized), onto the metallic braided layer 113. The hydrophobic barrier layer 120 and the inner polymeric layer 112 may be directly and/or covalently bonded together. Again, the heat energy of the extrusion process and/or the reflow/heat lamination process, if such is applied, may assist in forming such a direct and/or covalent bond between the hydrophobic barrier layer 120 and the inner polymeric layer 112.

Alternatively, in at least one embodiment, referring to FIG. 2, for example, a catheter shaft, such as catheter shaft 100, may be manufactured by co-extruding a first polymer, such as an amine-terminated PEBA, to a second polymer, such as an EFEP copolymer (which may be terminally-functionalized), to form the first polymer layer 110 and a second polymer layer 120. The co-extrusion process may be carried out with two synergically-controlled extruders to obtain desirable, respective thicknesses of the layers. As discussed above, the first polymer layer 110 may comprise outer and inner polymeric layers 111 and 112, respectively. As shown in FIG. 2, the hydrophobic barrier layer or second polymer layer 120 may form an outer layer of the catheter shaft 100 that is bonded, directly and/or covalently, for example, to the outer polymeric layer 111 of the first polymer layer 110. The heat energy of the co-extrusion process may assist in forming such a direct and/or covalent bond between the second polymer layer 120 and outer polymeric layer 111. Alternatively, referring to FIG. 3, the second polymer layer 120 may form the inner layer of the catheter shaft 100' that is bonded, directly and/or covalently, for example, to the inner polymeric layer 112 of the first polymer layer 110. Again, the heat energy of the co-extrusion process may assist in forming such a direct and/or covalent bond between the second polymer layer 120 and inner polymeric layer 112. Further, in at least one embodiment and referring to FIG. 4, another hydrophobic barrier layer or third polymer layer 130 may be formed by co-extruding a third polymer, such as an EFEP copolymer (which may be the same or similar as the second polymer discussed above), along with the first and second polymers. In such an embodiment, hydrophobic barrier layers 120 and 130 may form the interior and exterior layers of the catheter shaft 100" and may both be directly and/or covalently bonded to the layers 111, 112, respectively, of the first polymer layer 110. Again, the heat energy of the co-extrusion process may assist in forming such a direct and/or covalent bond between the second polymer layer 120 and outer polymeric layer 111 and between the third polymer layer 130 and the inner polymeric layer 112. Lastly, in at least one embodiment and referring to FIG. 5, the inner polymeric layer 112 of catheter shaft 100''' may be first extruded and then a metallic braided layer 113 may be formed by braiding stainless steel flat wire, for example, onto the inner polymeric layer 112. In such an embodiment, the hydrophobic barrier layer 120 and the outer polymeric layer 111 may be formed by a co-extrusion process such that the polymer of the hydrophobic barrier layer 120, EFEP copolymer (which may be terminally-functionalized), for example, is bonded, directly and/or covalently, for example, to the outer polymeric layer 111.

During clinical procedures, catheter shafts may be exposed to aqueous surroundings of the vessel and human anatomy for prolonged time, and any exposed polar polymeric materials of a catheter shaft may, as a consequence, unavoidably absorb water, which may act as a plasticizer for exposed polar polymeric shafts. Tests have shown that PEBA-based catheters, for example, that do not include a hydrophobic barrier layer, may absorb water at an amount of up to 2% by weight upon immersion into saline. The moisture absorbed into the materials may act as a plasticizer, potentially leading to decreases in the catheter shaft's mechanical strength and stiffness/rigidity. As a result, such shafts could exhibit mechanical softening phenomena over time, which could lead to decreases in mechanical strength, column stiffness, pushability, torqueability, and the like. As a consequence, this softening could lead to changes in end-use performance, such as compromised catheter shaft deliverability along a vessel and poor shaft maneuverability within the target human anatomy. Moreover, any such in-procedure performance changes could affect an operating physician's perception of use.

The hydrophobic barrier layer described above may be useful to prevent or resist water or any aqueous medium from being absorbed by the catheter shaft. As noted above, typically, catheter shafts are made of polar polymeric materials and providing a hydrophobic barrier layer may prevent the degradation of mechanical properties that may occur where the polar polymeric materials would have previously been exposed to an aqueous environment and absorb water and/or other fluids. Therefore, providing a hydrophobic barrier layer to the exterior of a catheter shaft may help minimize or eliminate the changes in shaft deliverability and/or maneuverability during a surgical procedure. Also, providing a hydrophobic barrier layer to the interior of a catheter shaft may help minimize or eliminate the changes in shaft deliverability and/or maneuverability due to saline from an irrigation lumen, either a central lumen or one or more such lumens in the wall of a catheter, for example. Additionally, because a hydrophobic barrier layer, such as the second polymer layer 120 seen in FIG. 2, for example, may be directly and/or covalently bonded to the polar polymer layer, such as the first polymer layer 110 in FIG. 2, for example, the hydrophobic barrier layer may not delaminate or separate from the polar polymer layer during use.

Alternative catheter shaft materials to an EFEP copolymer or copolymers include other non-polar polymers, such as polyolefins (e.g., high-density polyethylene ("HDPE"), low-density polyethylene ("LDPE"), linear low-density polyethylene ("LLDPE"), polypropylene ("PP"), etc.) and engineering fluoropolymers (e.g., perfluoroalkoxy ("PFA"), fluorinated ethylene propylene ("FEP"), polyvinylidene fluoride ("PVDF"), ethylene tetrafluoroethylene ("ETFE"), etc.) as these other non-polar polymers have inherent chemical resistance and moisture barrier properties. However, those non-polar polymers generally have undesirable thermal or mechanical properties for making a catheter body, and are chemically inert such that they can't be conveniently assembled with other catheter components using secondary manufacturing technologies such as adhesive bonding, welding, and the like. To largely maintain the mechanical flexibility and thermal behaviors of a catheter shaft in the human anatomy, polar polymers may still need to be used for at least a portion of the catheter shaft. To allow the above-listed non-polar polymeric materials to chemically bond onto the catheter shaft, however, chemical functionalization, preferably at the non-polar polymers' ending groups, may be helpful. If one or more functionalized, non-polar polymeric materials are used as a thin moisture barrier layer(s), or hydrophobic barrier layer(s), for at least some or all surfaces of the catheter that are in contact with an aqueous environment, the catheter should be well protected from water penetration.

EXPERIMENTAL EXAMPLES

Various non-limiting experimental examples utilizing functionalized EFEP copolymers as a hydrophobic barrier layer for a catheter shaft are described below.

Example #1

Using FIG. 5 as a reference, a non-reactive polar, non-fluorine containing polymeric material, poly(ether block amide) ("PEBA") copolymer (specifically, PEBAX® 7233 (sold by Arkema Inc., Philadelphia, Pa., USA) loaded with 30% barium sulfate by weight), was extruded as the inner polymeric layer 112 over a supportive, acetal monofilament (not shown) defining the inner diameter of the catheter shaft 100'''. Then, eight strands of stainless steel flat wire having a size of approximately 0.001" by 0.004" were braided onto the inner polymeric layer 112 at a one-under-two, one-over-two pattern to prepare the metallic braided layer 113, over which an outer polymeric layer 111 using the same polymeric material used to extrude the inner polymeric layer 112 (PEBAX® 7233 loaded with 30% barium sulfate). Finally, a functionalized FCP, EFEP copolymer (specifically, NEOFLON™ RP-5000 sold by Daikin America, Inc.), was extruded onto the outer polymeric layer 111 via a sequential mono-extrusion technique, discussed above, to form the hydrophobic barrier layer 120 on the outer circumference of the catheter shaft 100'''. In this example, the hydrophobic barrier layer 120 did not appear to covalently bind to the outer polymeric layer 111 as flexion testing of the shaft 100''' led to delamination of the hydrophobic barrier layer 120 from the outer polymeric layer 111.

Example #2

Using FIG. 5 as a reference, a non-reactive polar, non-fluorine containing polymeric material, PEBA copolymer compound (PEBAX® 7233 loaded with 30% barium sulfate by weight), was extruded as the inner polymeric layer 112 over a supportive, acetal monofilament (not shown) defining the inner diameter of the catheter shaft 100'''. Then, sixteen strands of stainless steel flat wire having the size of approximately 0.001" by 0.004" were braided onto the inner polymeric layer 112 at a one-under-two, one-over-two pattern to prepare the metallic braided layer 113, over which an outer polymeric layer 111 was extruded. The outer polymeric layer 111 was extruded from a different polymeric material than that used for the inner layer 112, RILSAN® BESNO nylon-11 homopolymer (sold by Arkema Inc.) filled with 30 wt. % barium sulfate. Finally, a functionalized FCP, EFEP copolymer (specifically, NEOFLON™ RP-4200 sold by Daikin America, Inc.), was extruded onto the outer polymeric layer 111 via a sequential mono-extrusion technique, discussed above, to form the hydrophobic barrier layer 120 on the outer circumference of the catheter shaft 100'''. In this example, the hydrophobic barrier layer 120 did not appear to covalently bind to the outer polymeric layer 111 as flexion testing of the catheter shaft 100''' led to the hydrophobic barrier layer 120 delaminating from the outer polymeric layer 111.

Example #3

Using FIG. 6 as a reference, a modified PEBA copolymer containing amine ending groups, VESTAMID® BS-1145, was extruded as the inner polymeric layer 112 over a supportive, acetal monofilament (not shown) defining the inner diameter of the catheter shaft 100''''. Then, eight strands of stainless steel flat wire having the size of approximately 0.001" by 0.004" were braided onto the inner polymeric layer 112 at a one-under-two, one-over-two pattern to prepare the metallic braided layer 113, over which a functionalized FCP, EFEP copolymer (specifically, NEOFLON™ RP-4200 sold by Daikin America, Inc.), was directly extruded to form the hydrophobic barrier layer 120. In this example, the hydrophobic barrier layer 120 was immediately adjacent to the metallic braided layer 113 and an additional outer polymeric layer (such as layer 111 seen in FIG. 5) was not required. Further, in this example, the hydrophobic barrier layer 120 appeared to covalently bind to the inner polymeric layer 112 through the braid openings 114 as flexion testing of the catheter shaft 100'''' did not lead to delamination of the hydrophobic barrier layer 120 from the inner polymeric layer 112.

Example #4

Using FIG. 5 as a reference, the inner polymeric layer 112 and the metallic braided layer 113 were prepared as described above in Examples #1 and #2. Functionalized EFEP copolymer (NEOFLON™ RP-5000, Daikin America, Inc.) was co-extruded with a barium sulfate-filled, radiopaque PEBA copolymer (PEBAX® 7233, Arkema Inc.) compound over the metallic braided layer 113 to form the outer polymeric layer 111 (comprising PEBAX® 7233) and the hydrophobic barrier layer 120 (comprising NEOFLON™ RP-5000). Accordingly, in this example, the outermost surface of the catheter shaft 100''' solely consisted of the functionalized EFEP copolymer providing hydrophobic protection to the catheter shaft 100''' in the form of the hydrophobic barrier layer 120. In this example, the hydrophobic barrier layer 120 did not appear to covalently bind to the outer polymeric layer 111 as flexion testing of the catheter shaft 100''' led to delamination of the hydrophobic barrier layer 120 from the outer polymeric layer 111.

Example #5

Using FIG. 5 as a reference, the inner polymeric layer 112 and the metallic braided layer 113 were prepared as described above in Examples #1 and #2. Functionalized EFEP copolymer (NEOFLON™ RP-5000) was coextruded with a functionalized PEBA copolymer with amine ending groups (VESTAMID® BS-1145) over the metallic braided layer 113 to form the outer polymeric layer 111 (comprising VESTAMID® BS-1145) and the hydrophobic barrier layer 120 (comprising NEOFLON™ RP-5000). Accordingly, in this example, the hydrophobic barrier layer 120 formed the outermost surface of catheter shaft 100''' to provide hydrophobic protection thereto via the functionalized EFEP copolymer of the hydrophobic barrier layer 120. In this example, the hydrophobic barrier layer 120 appeared to covalently bind to the outer polymeric layer 111 as flexion testing of the catheter shaft 100''' did not lead to delamination of the hydrophobic barrier layer 120 from the outer polymeric layer 111.

Example #6

Using FIG. 6 as a reference, a functionalized EFEP copolymer (NEOFLON™ RP-5000) was extruded as the inner polymeric layer 112 over a supportive, acetal monofilament (not shown) defining the inner diameter of the catheter shaft. Then, eight strands of stainless steel flat wire having the size of approximately 0.001" by 0.004" were braided onto the inner polymeric layer 112 at a one-under-two, one-over-two pattern to prepare the metallic braided layer 113, over which the hydrophobic barrier layer 120 was extruded using the same polymeric material as the inner polymeric layer 112 (NEOFLON™ RP-5000). In this example, the hydrophobic barrier layer 120 appeared to covalently bind to the inner polymeric layer 112 (which also was hydrophobic) as flexion testing of the catheter shaft 100''' did not lead to delamination of the hydrophobic barrier layer 120 from the inner polymeric layer 112.

Example #7

An inner polymeric layer (comprising a non-reactive PEBA copolymer, PEBAX® 7233) and a metallic braided layer were prepared as described above in Examples #1 and #2. For the purposes of this example, the combination of the metallic braided layer on the inner polymeric layer is referred to as the braided inner polymeric layer. An EFEP tube was extruded from NEOFLON™ RP-5000 such that the inner diameter of the EFEP tube was slightly larger than the outer diameter of the braided inner polymeric layer. The EFEP tube was next placed over the braided inner polymeric layer and then a polytetrafluoroethylene ("PTFE") shrink tube was applied over the EFEP tube. Finally, heat was applied over the PTFE shrink tube at a temperature higher than the melting point of the PEBA copolymer but slightly lower than the melting point of the EFEP copolymer to incorporate all of the tubular components into a bonded composite structure via a heat lamination or reflow process of the PEBA copolymer. Then, the PTFE shrink tube was removed. In this example, the outer EFEP layer did not appear to covalently bind to the PEBA copolymer layer as flexion testing of the catheter shaft 100''' led to delamination of the EFEP tube layer from the PEBA copolymer layer.

Example #8

Using FIG. 5 as a reference, the inner polymeric layer 112 and the metallic braided layer 113 were prepared as described above in Examples #1 and #2. Functionalized EFEP copolymer (NEOFLON™ RP-5000, Daikin America, Inc.) was coextruded with a semi-flexible nylon-11 (RILSAN® BESNO, Arkema Inc.) polymer compound filled with 30 wt. % barium sulfate over the metallic braided layer 113 to form the outer polymeric layer 111 (comprising RILSAN® BESNO) and the hydrophobic barrier layer 120 (comprising NEOFLON™ RP-5000). Accordingly, in this example, the outermost surface of the catheter shaft 100''' comprised functionalized EFEP copolymer to provide hydrophobic protection to the catheter shaft 100''' in the form of the hydrophobic barrier layer 120. In this example, the hydrophobic barrier layer 120 did not appear to covalently bind to the outer polymeric layer 111 as flexion testing of the catheter shaft 100''' led to delamination of the hydrophobic barrier layer 120 from the outer polymeric layer 111. Note that RILSAN® BESNO P20 TL (Arkema Inc.), a grade of nylon-11 polymer compound containing a plasticizer to make it more flexible than RILSAN® BESNO, could also be substituted for the RILSAN® BESNO used in this and/or other examples described above because RILSAN® BESNO P20 TL should have the same or similar melt-adhesion results as RILSAN® BESNO due to the fact that RILSAN® BESNO and BESNO P20 TL have the same or similar resin chemistry.

The results of the above-described experimental examples are tabulated below. The table shows the specific composition of the polymer layer initially contacting the hydrophobic barrier layer ("HBL"), which comprised a terminally-functionalized EFEP copolymer (either NEOFLON™ RP-4200 or NEOFLON™ RP-5000), and the delamination results of the catheter shaft flexion testing, that is whether the HBL delaminated from the polymer layer to which it initially contacted during bending.

| Example # | Polymer Layer Contacting the HBL | Delamination (Yes/No) |
|---|---|---|
| 1 | PEBAX® 7233 | Yes |
| 2 | RILSAN® BESNO | Yes |
| 3 | VESTAMID® BS-1145 | No |
| 4 | PEBAX® 7233 | Yes |
| 5 | VESTAMID® BS-1145 | No |
| 6 | NEOFLON™ RP-5000 | No |
| 7 | PEBAX® 7233 | Yes |
| 8 | RILSAN® BESNO | Yes |

Based on the above-tabulated results, the polymer layers contacting the HBL that did not delaminate, and therefore likely covalently bound to the HBL were VESTAMID® BS-1145 and NEOFLON™ RP-5000. As discussed above, VESTAMID® BS-1145 is an amine-terminated PEBA and NEOFLON™ RP-5000 is a terminally-functionalized EFEP copolymer. Further, the HBL was also a terminally-functionalized EFEP copolymer (either NEOFLON™ RP-4200 or NEOFLON™ RP-5000). Accordingly, the end functional groups on the terminally-functionalized EFEP copolymer appeared to covalently bind to the end functional groups on the same or similar copolymer, or to the end amine groups on the amine-terminated PEBA leading to a set of layers that did not delaminate yet had hydrophobic protection provided by the hydrophobic barrier layer.

Additionally, EFEP copolymers such as the NEOFLON™ RP resins discussed above were found to have good melt processability and adhesive properties to hot PEBAX®, nylon-11, and functionalized PEBA copolymer melts and metal surfaces under normal melt processing temperatures from about 210° C. to 260° C. Moreover, the functionalized EFEP resins appeared to maintain their inherent hydrophobicity, evident by little to no effects on its mechanical properties after molded samples were completely immersed in a saline bath for 24 hours. Accordingly, functionalized EFEP copolymer appears to be a suitable hydrophobic barrier material for use in various catheter shafts.

Additional uses of a composition according to the present disclosure are envisioned. For example, in various embodiments, a composition may comprise a first polymer bonded to a second polymer. The first polymer may comprise a reactive polar polymer, which may be amine-terminated, such as an amine-terminated PEBA, and the second polymer may comprise an EFEP copolymer, which may be functionalized, such as a terminally-functionalized EFEP copolymer, as discussed above above. Such a composition may be useful to provide a hydrophobic barrier layer along with the mechanical benefits of the reactive polar polymer to a number of products and/or processes, such as, but not limited to medical devices, consumer products, food packaging, industrial processing, and the like, for example.

Although various embodiments have been described above with a certain degree of particularity, those skilled in the art could make numerous alterations to the disclosed embodiments without departing from the spirit or scope of this disclosure. For example, different products/devices than those described herein may benefit from a hydrophobic barrier layer. All directional references (e.g., proximal, distal, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter comprising an elongated structure, wherein the elongated structure has a distal portion and a proximal portion, wherein:
the proximal portion comprises a handle operably connected to the proximal end of the elongated structure;
the distal portion comprises a shaft, wherein the shaft comprises a first polymer layer bonded to a second hydrophobic polymer layer, wherein the first polymer layer comprises an outer polymer sub-layer and an inner polymer sub-layer, wherein the second hydrophobic polymer layer comprises an ethylene-perfluoroethylenepropylene ("EFEP") copolymer, and further wherein the shaft comprises a metallic braided layer between the outer polymer sub-layer and the inner polymer sub-layer, wherein the EFEP copolymer comprises end functional groups selected from the group consisting of carboxyl groups, carbonate groups, carboxyl halide groups, and carbonyl halide groups, and further wherein the first layer comprises a reactive polar polymer, wherein the reactive polar polymer comprises an amine-terminated polar polymer; and
wherein the catheter is configured to be inserted into a patient's body.

2. The catheter of claim 1, wherein the first polymer layer is directly bonded to the second polymer layer.
3. The catheter of claim 2, wherein the first polymer layer is covalently bonded to the second polymer layer.
4. The catheter of claim 1, wherein the amine-terminated polar polymer comprises an amine-terminated poly(ether block amide) ("PEBA").
5. The catheter of claim 1, wherein the second polymer layer is an outer layer of the catheter.
6. The catheter of claim 1, wherein the second polymer layer is an inner layer of the catheter.
7. The catheter of claim 1, further comprising a third polymer layer that comprises an EFEP copolymer.
8. The catheter of claim 7, wherein the third polymer layer is bonded to the first polymer layer.
9. The catheter of claim 1, wherein the first polymer layer is internal to the second polymer layer.
10. The catheter of claim 1, wherein the distal portion further comprises an electrode.
11. The catheter of claim 1, wherein the EFEP copolymer has a melting point between 160° C. and 220° C.
12. A catheter comprising an elongated structure, wherein the elongated structure has a distal portion and a proximal portion, wherein:
the proximal portion comprises a handle operably connected to the proximal end of the elongated structure;
the distal portion comprises a shaft, wherein the shaft comprises a first polymer layer bonded to a second hydrophobic polymer layer, wherein the first polymer layer comprises an outer polymer sub-layer and an inner polymer sub-layer, and wherein the first polymer layer comprises a reactive polar polymer, wherein the reactive polar polymer comprises an amine-terminated polar polymer, and further wherein the shaft comprises a metallic braided layer between the outer polymer sub-layer and the inner polymer sub-layer; and
wherein the catheter is configured to be inserted into a patient's body.
13. The catheter of claim 12, wherein the amine-terminated polar polymer comprises an amine-terminated poly (ether block amide) ("PEBA") selected from the group consisting of VESTAMID BS-1144 and VESTAMID BS-1145.
14. The catheter of claim 12, wherein the second polymer layer comprises a non-polar polymer.
15. The catheter of claim 12, wherein the first polymer layer is covalently bonded to the second polymer layer.

* * * * *